United States Patent [19]

Howard et al.

[11] 4,331,026
[45] May 25, 1982

[54] INDENTER-TYPE HARDNESS TESTING APPARATUS

[75] Inventors: Bruce S. Howard; William O. Walters, both of Seattle, Wash.

[73] Assignee: The Boeing Company, Seattle, Wash.

[21] Appl. No.: 168,626

[22] Filed: Jul. 14, 1980

[51] Int. Cl.³ .................. G01C 25/00; G01N 3/42
[52] U.S. Cl. .................................. 73/81; 73/1 R; 340/680; 364/571
[58] Field of Search .............. 73/81, 1 R, 12; 364/571, 550

[56] References Cited

U.S. PATENT DOCUMENTS

| | | | |
|---|---|---|---|
| 3,153,338 | 10/1964 | Keesattel | 73/78 |
| 3,302,454 | 2/1967 | Keesattel | 73/78 |
| 3,308,476 | 3/1967 | Keesattel | 73/78 |
| 3,324,458 | 6/1967 | MacArthur | 340/172 |
| 3,425,263 | 2/1969 | Elliott et al. | 73/12 |
| 3,453,862 | 7/1969 | Elliott et al. | 73/12 |
| 3,720,813 | 3/1973 | Badessa | 73/1 R X |
| 3,759,085 | 9/1973 | Wilson et al. | 73/12 |
| 3,788,466 | 1/1974 | Wilson et al. | 73/12 |
| 3,930,248 | 12/1975 | Keller | 100/99 X |
| 4,004,450 | 1/1977 | Yakshin et al. | 73/12 |
| 4,023,396 | 5/1977 | Yakshin et al. | 73/12 |
| 4,030,339 | 6/1977 | Yakshin et al. | 73/12 |
| 4,034,603 | 7/1977 | Leeb et al. | 73/79 |
| 4,055,842 | 10/1977 | Yakshin et al. | 73/12 |
| 4,094,188 | 6/1978 | Bellouin et al. | 73/81 |
| 4,111,039 | 9/1978 | Yamawaki et al. | 73/81 |
| 4,163,393 | 8/1979 | Gutierrez et al. | 73/12 X |
| 4,263,803 | 4/1981 | Burkhardt | 73/1 R |

OTHER PUBLICATIONS

Publ. Wilson Instrument Div., "Production Rockwell Hardness Testor", Acco Brochure, 1977.

Publ. Barber-Colman Brochure-"Impressor Models", GYZJ 934-1, etc.

Primary Examiner—Daniel M. Yasich
Attorney, Agent, or Firm—Christensen, O'Connor, Johnson & Kindness

[57] ABSTRACT

A material hardness testing apparatus is provided, for use in quality control of production materials and parts, in which a pneumatically actuated indenter probe, incorporating an LVDT displacement transducer, is coupled by an analog-to-digital converter to a microprocessor-based computer that controls the cyclic actuation of the indentor probe, and processes indenter measurement data received from the LVDT transducer. The pneumatically actuated indenter probe includes pneumatic control means for providing independently adjustable control over the rates of probe impact and retraction in order to achieve consistent hardness measurements from cycle to cycle, together with relatively rapid displacement cycling of the indenter probe. The microprocessor-based computer incorporates a recalibration processor which automatically causes the testing apparatus to branch into a recalibration routine after a predetermined period of operation. During such recalibration, the apparatus semi-automatically tests and compares the measured hardness of one or more reference specimens with hardness values stored in memory and either disables the testing apparatus when the measured hardness deviates from the standard by a predetermined percentage amount, or stores in memory the difference between the measured hardness and the standard and enables the apparatus to continue with further testing. In each succeeding test, the apparatus automatically subtracts or adds the magnitude of the memorized difference to the raw measured hardness value to correct the hardness reading displayed by the apparatus.

18 Claims, 11 Drawing Figures

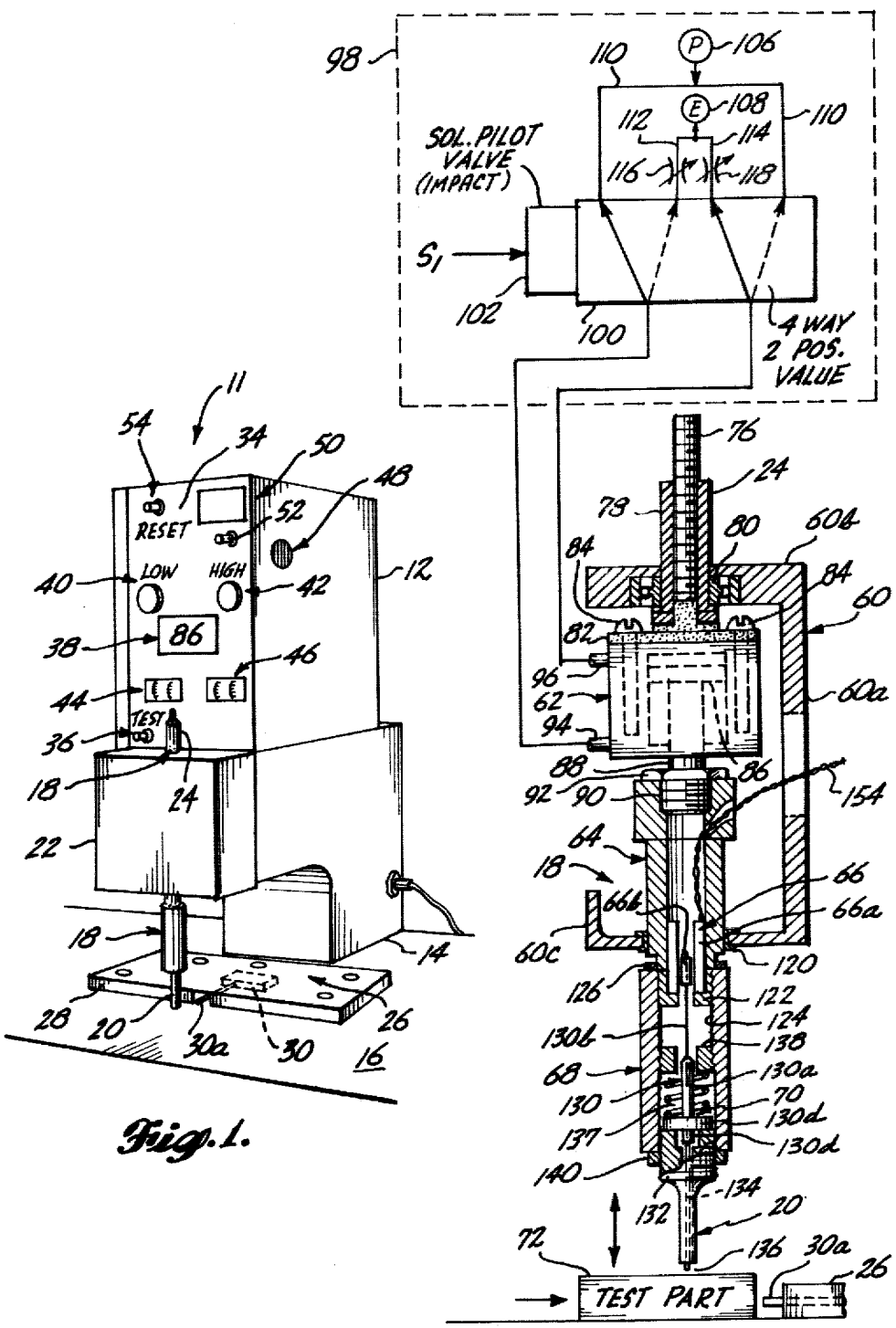

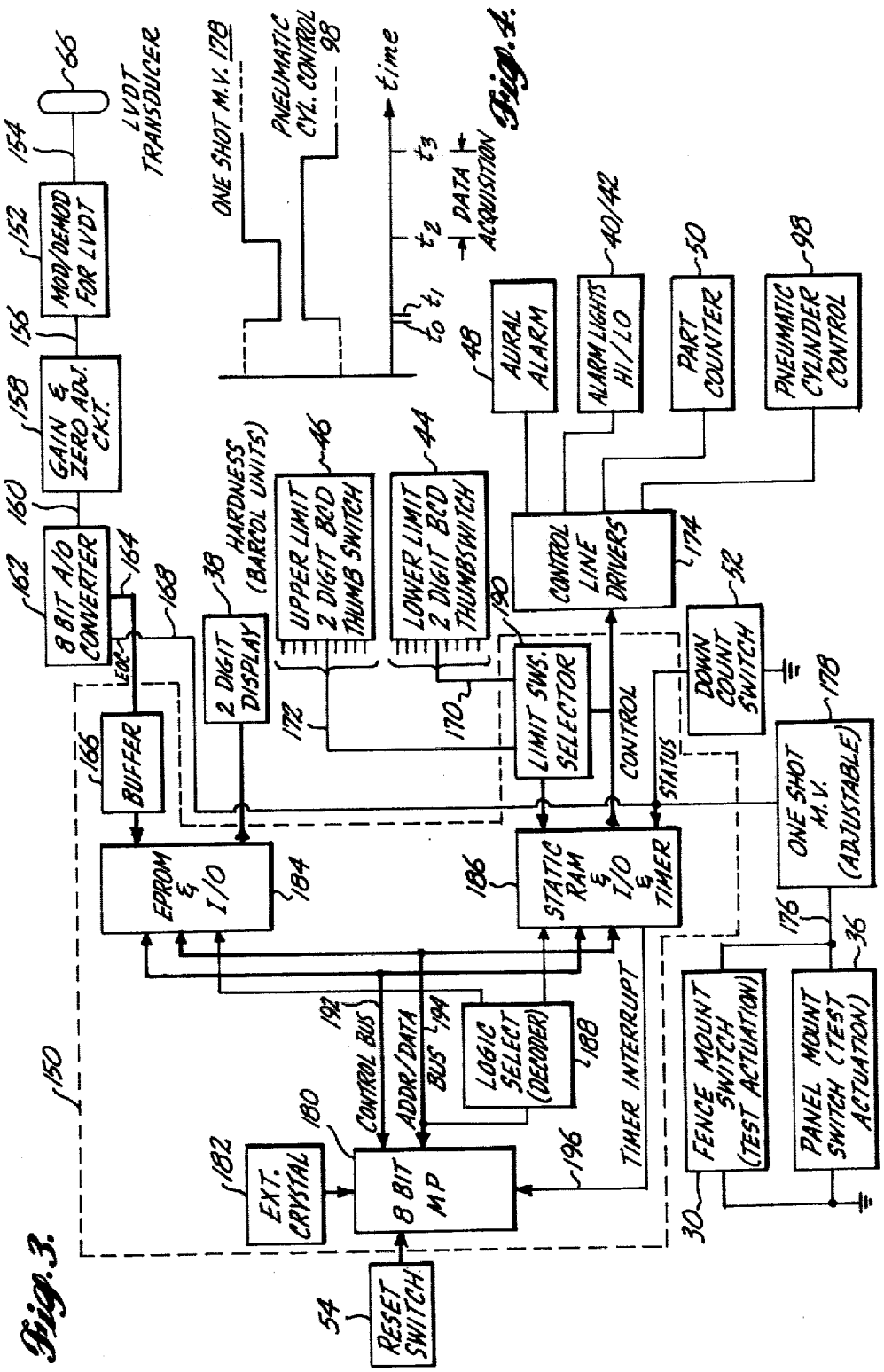

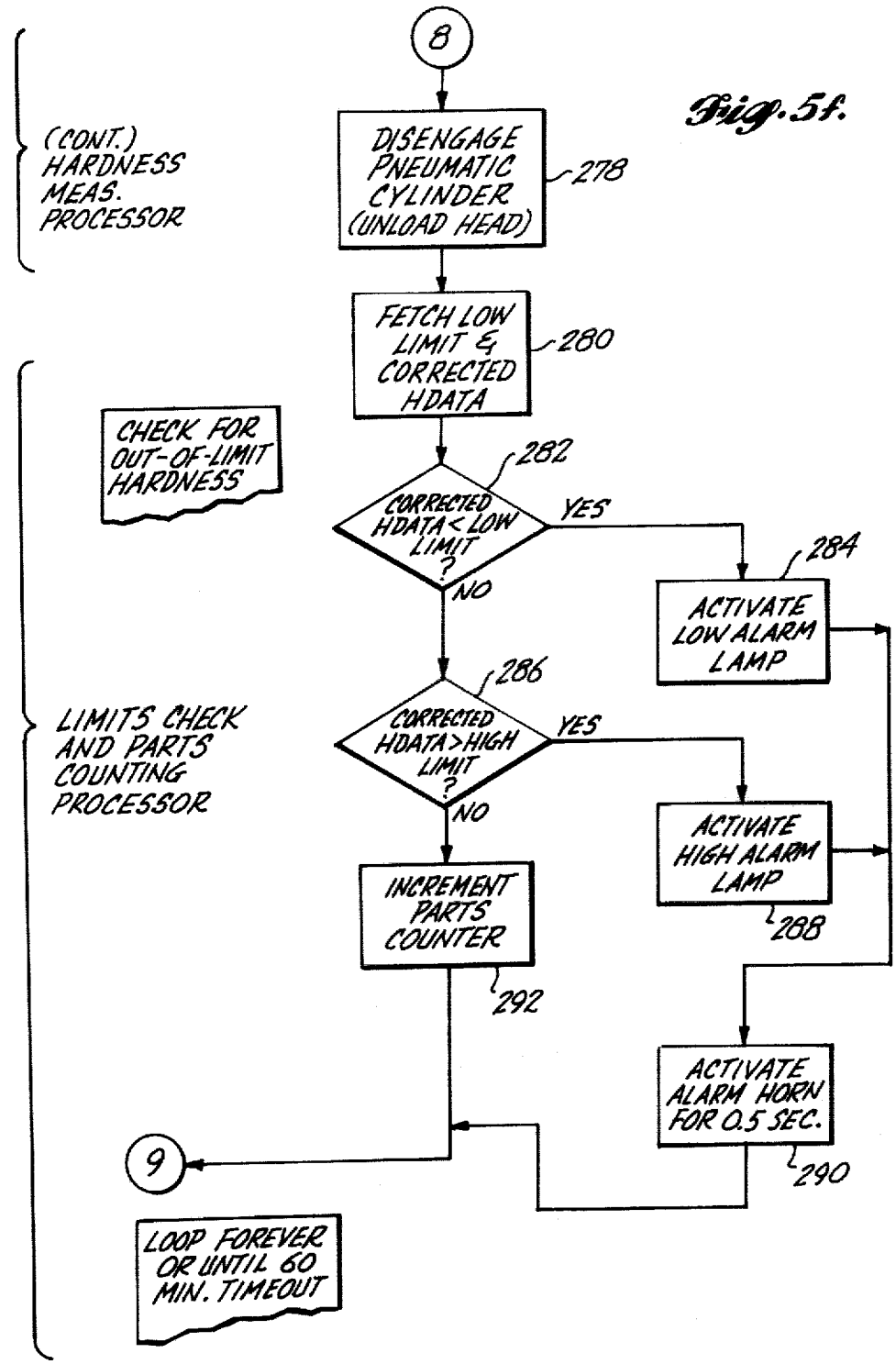

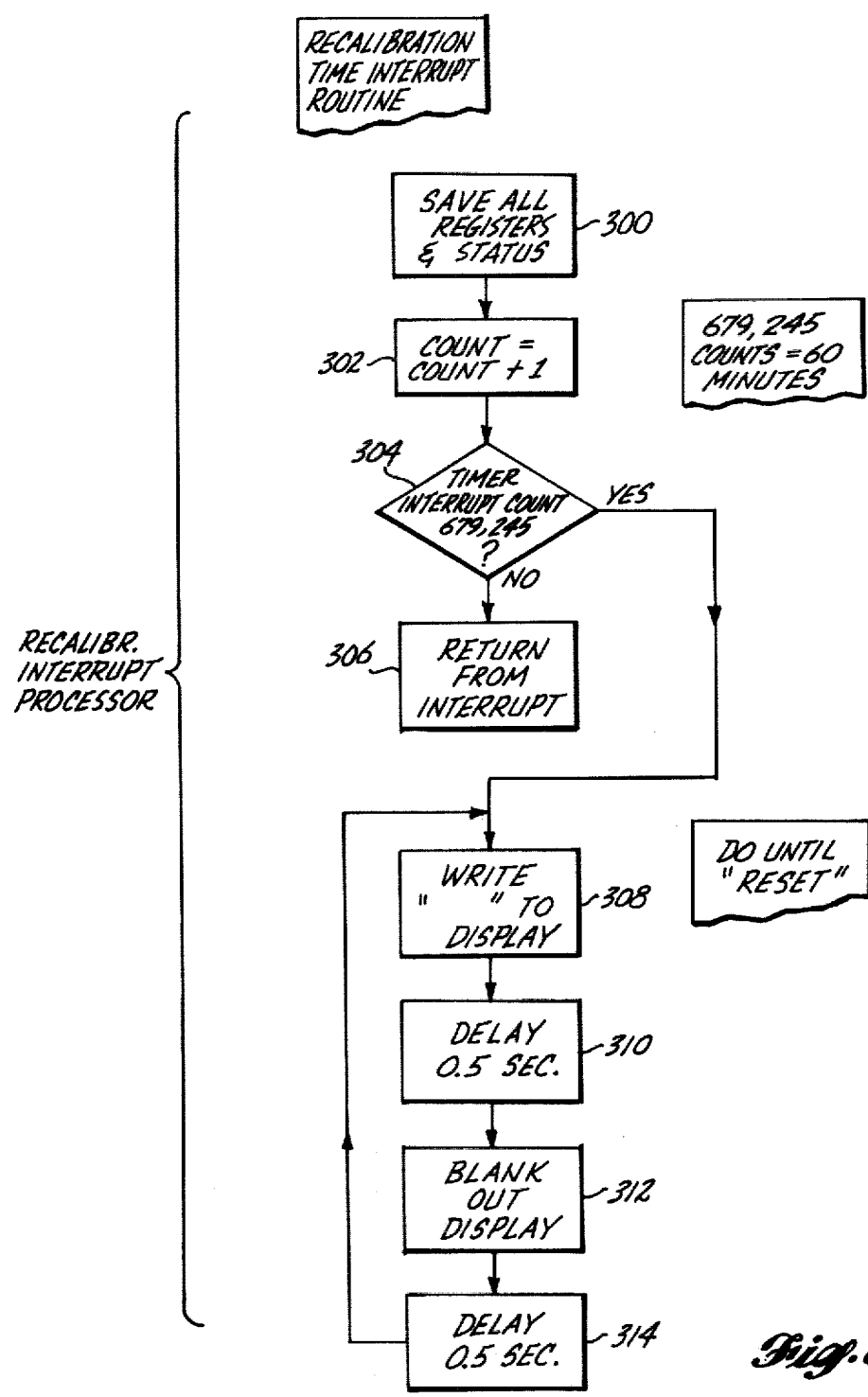

INDENTER-TYPE HARDNESS TESTING APPARATUS

BACKGROUND OF THE INVENTION

The invention pertains to automatic and semi-automatic hardness testing equipment and more particularly to testing instruments that measure hardness by subjecting the test parts to the impact of an indenter probe and then electrically sense the depth of indenter penetration.

In controlling the quality of production parts, there is often a need to measure, on a routine production basis, the hardness of materials, especially metals, that are incorporated into a manufactured article. For example, in the fabrication of aircraft parts made of various lightweight alloys of aluminum, the hardness of these alloys is tested to verify that the part is made of the proper mixture of alloyed components and has the desired heat treatment. More particularly, it has heretofore been discovered that a reliable correlation exists between the composition of an aluminum alloy having a given heat treatment (temper), and the combined hardness and the electrical conductivity of the alloy. Thus, by measuring both the hardness and the electrical conductivity of the production part or stock material, empirically generated tables can be referred to verify that the particular alloy has the proper mixture of alloyed metals, and the correct temper.

Known testing devices are available for individually measuring hardness and electrical conductivity pursuant to the above characterized quality control test. The present invention pertains to an improvement in a testing apparatus for measuring material hardness. Prior to the present invention, hardness has been measured by manual, automatic and semi-automatic testers. One popular tester of the manually actuated type provides an indenter pin slidably mounted in a handheld housing, and a displacement dial indicator also mounted on the housing and mechanically linked to the slidable indenter pin. The operator manually forces the tester, including the slidable indenter pin, against the face of the part to be tested, causing the indenter pin to penetrate the material. This type of tester is generally referred to as a single step indenter because the tested material is subjected to the impact of a single stroke of the indenter pin tip. The degree of penetration of the indenter pin is converted by the mechanical linkage to the indicator dial which measures the amplitude of the penetration, and hence provides an indication of the material hardness. In some versions, the penetration is measured by electromechanical means. In this kind of tester, the indenter pin has a specially contoured tip, which when used in a tester of this type, has proven to provide a usable degree of correlation between the dial indicated hardness and other more scientifically based, and more precise hardness scales such as those resulting from Rockwell, Brinell and scleroscope testing procedures and/or devices.

Although one of the other hardness testing procedures, such as Rockwell or Brinell would provide a more accurate and consistent measurement of hardness, the use of Rockwell, Brinell and other multiple step tests is undesirable for performing quality control testing of aluminum alloys on a production basis, where a large number of parts must be tested quickly and easily, by nonscientifically trained personnel.

For this purpose, manually actuated, one step indenter testers have been preferred for production testing. While faster, currently available one step indenter-type testers are deficient in terms of producing consistent and hence accurate hardness measurements. Moreover, when such a device is manually, as opposed to automatically actuated, operator fatigue has been found to enter into the accuracy of the testing, especially after an operator has tested a large number of parts and the manually dependent impact force on the indenter pin becomes erratic. The problem of achieving consistent results becomes even more acute, when the tester is employed to determine the hardness of materials that exhibit an impact rate dependent hardness. Some materials, such as aluminum and various aluminum alloys, show a marked change in hardness, as a function of the rate at which the indenter tip is driven toward and into the material. At an extremely high rate of impact, the creep of the material is minimal and hence the indenter tip does not penetrate the metal as much as when the impact rate is decreased to afford time for the material to yield as the tip penetrates into the test part.

Another shortcoming of available hardness testers, especially the one step, indenter impact-types, is the difficulty in maintaining an acceptable level of calibration of the tester over the long intervals of time that are typically associated with the testing of production parts. Frequent recalibration of the tester is required which involves keeping track of the number of test cycles that have occurred since the last calibration, and then at the end of that interval, stopping the testing procedure and recalibrating the device by an adjustment provided in the mechanical or electromechanical coupling between the indenter tip and the displacement indicator dial or readout. While frequent recalibration of hardness testers of this general type is probably unavoidable, the difficulty involved in readjusting these devices, not only slows the testing operation down, but in some cases requires that the recalibration be performed by different, more skilled personnel than those which are performing the routine production testing.

Accordingly it is an object of the invention to provide a one step, indenter impact-type hardness testing apparatus, suitable for use in the rapid testing of large numbers of production parts or materials, and is characterized by the capability of yielding consistent hardness measurements that are independent of variations in the indenter impact force usually associated with operator actuated indenter devices.

Still another object of the invention is to provide a hardness testing apparatus of the above characterized type capable of achieving consistent hardness measurements and which can be operated at a greater cyclic speed than is achievable by manually actuated hardness testers of this kind.

A further object of the invention is to provide a one step, indenter impact hardness tester which is automatically controlled so that after predetermined usage, a recalibration processor provides in a semi-automatic manner, for two different levels of recalibration, one of which is automatically implemented during succeeding test cycles to minimize the apparatus down time, and the other of which requires a shutdown of the apparatus for servicing.

SUMMARY OF THE INVENTION

A fluid actuated electrically sensed indenter probe is provided with fluid control means for independently adjusting the rates of the impact and retraction strokes of the probe. Cooperating with the indenter probe is a microprocessor-based computer having control and test signal interfacing with the fluid actuated probe and functioning together with the fluid control to automatically drive the probe in an impact stroke, and thereafter to withdraw the probe in a retraction stroke. Signal processors incorporated in the microprocessor-based computer receive and process analog-to-digital converted data developed by a position sensing transducer within the probe and produce a hardness reading, and/or an indication of whether the measured hardness falls inside or outside of acceptable, preset hardness limits.

The microprocessor-based computer includes a recalibration processor involving two levels of semiautomatic recalibration. A timer measures the duration of operating time of the test apparatus and afer a predetermined period of usage, causes the data and control signal processors of the computer to branch to a recalibration processing routine. Cooperating with an operator inserted calibration block, the apparatus automatically measures and compares the results of the measured hardness with a stored value of the known hardness of the calibration blocks. Depending upon the magnitude of the deviation, the recalibration processor either causes an automatic disablement of the apparatus to allow for a major recalibration servicing, or returns the control of the apparatus to the test data and control processors of the apparatus for resuming routine testing. Prior to returning the apparatus to its routine testing mode, the recalibration routine processor stores the magnitude and sign of the measured deviation from the hardness standard, and during each succeeding test cycle, causes the hardness data to be corrected by the measured error, hence automatically performing a lesser degree of recalibration of the apparatus, without losing production time due to apparatus down time associated with a major recalibration requirement.

Preferably, the test apparatus also incorporates limit setting and associated data processor means for comparing the measured hardness with preset limits, and actuating "high/low" indicators in accordance with such comparison. A tested parts counter is also preferably incorporated in the apparatus for automatically counting each actuation of the indenter probe, and a display is provided indicating the accumulated tested parts count.

Further, in accordance with the preferred embodiment, a head assembly that incorporates the indenter probe and the associated fluid actuator is constructed so as to provide a manual adjustment of the probe to part distance, without disturbing a spring bias force internally of the probe that is used to calibrate the test apparatus. Also, the probe is preferably constructed so as to provide for adjusting the calibration spring pressure independently of a zero output position of an electromechanical position transducer that senses the depth of indenter tip penetration.

To provide a complete disclosure of the invention, reference is made to the appended drawings and follwing description of one particular and preferred embodiment.

BRIEF DESCRIPTION OF THE DRAWINGS

FIG. 1 is a perspective view of the indenter-type hardness measuring apparatus shown mounted on a work bench.

FIG. 2 is a composite schematic and sectional view of a pneumatic control and associated indenter probe head assembly, in which the latter is shown partly in vertical section.

FIG. 3 is a detailed block diagram of the internal circuity of the testing apparatus of FIG. 1, in which such internal circuitry incorporates a microprocessor-based computer.

FIG. 4 is a waveform diagram showing the timing relationship between certain salient signals occurring in the circuitry shown in FIG. 3.

FIG. 6 is another flowchart, showing a semiautomatic, timed recalibration interrupt routine that is programmed into the above-mentioned computer and is associated with the signal processing shown in FIGS. 5a-f.

DETAILED DESCRIPTION

Figure 5A:
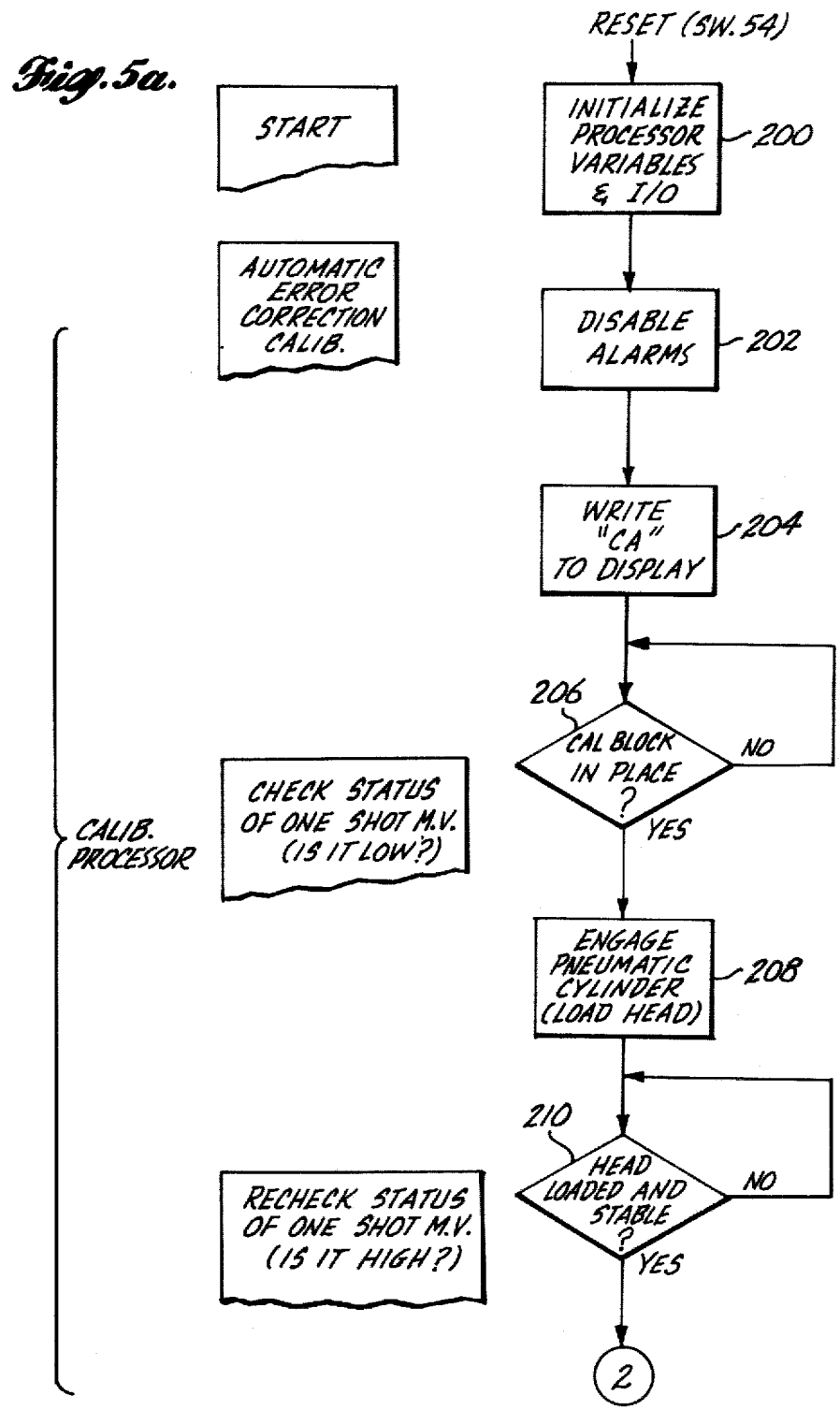
FIGS. 5a, b, c, d, e and f collectively constitute the flowchart of the processing performed by the programmed microprocessor-based computer referred to above and shown in the block diagram of FIG. 3.

With reference to FIG. 1, an indenter-type hardness testing apparatus 11 incorporating the principles of the invention is shown to include a housing 12 supported by a base 14 of inverted L-shape which in turn is fastened to the top of a workbench 16. A pneumatically actuated indenter probe head assembly 18 is mounted to base 14 adjacent the front thereof so that the head assembly which is elongated, is vertically oriented and has a lower probe tip 20 overlying a workpiece receiving area of bench 16. A cover 22 partially obscures head assembly 18 at a location where a mounting bracket of assembly 18 is secured to base 14. An upper end 24 of assembly 18 projects above the cover 22 and is provided with a thumbscrew height adjustment for manually varying the elevation separating probe tip 20 of assembly 18 and the surface of bench 16 as described in greater detail below in connection with FIG. 2.

A fence assembly 26 is mounted on the surface of bench 16 between base 14 and probe tip 20 to provide an indexing surface along the foward fence edge 28 so that a test part can be shoved into abutment with surface 28 to place the part immediately under probe tip 20. A microswitch 30 (shown by hidden lines) is mounted in fence assembly 26 and includes an actuating arm 30a that projects forwardly of assembly 26 and protrudes through an opening provided in surface 28 so that a test part will actuate switch 30 when inserted into test position. Switch 30 provides for actuating a test cycle automatically in response to the operator inserting the part to be tested.

The various control switches, indicator lamps and alpha-numeric displays of apparatus 11 are mounted on a control panel disposed as the forward face of housing 12 above and somewhat behind the location of probe head assembly 18. Included on control panel 34 are: a pushbutton test switch 36 for providing an alternative means of initiating a test cycle in conjunction with microswitch 30; a two digit alpha-numeric hardness display 38; low and high indicator lamps 40 and 42, respectively, for warning the operator that the tested part falls outside low and high hardness limits preset by using two digit thumbswitches 44 and 46, respectively; an audible alarm 48 such as a horn, mounted on a side wall of housing 12 adjacent panel 34; a six digit counter display 50 for displaying a running total of the number of parts tested and an associated count decrementing switch 52 for correcting the count shown on display 50; and a system reset switch 54. As described in greater detail hereinafter, dispaly 38 is an alpha-numeric display that in addition to presenting the hardness number, in Barcol units, displays certain letter and symbol codes in conjunction with the recalibration of apparatus 11 to indicate special operating conditions of the system. Audible alarm 48 is energized when the peset hardness limits have been exceeded either on the low or high end and thus will operate whenever low indicator lamp 40 or high indicator lamp 42 are turned on. Reset switch 54 is used to reset the system in cooperation with a recalibration routine that is semi-automatically carried out at the end of a fixed time interval that is determined by the microprocessor-based computer, the operation of which is described more fully below in connection with FIG. 3.

With reference to FIG. 2, probe head assembly 18 includes a mounting bracket 60, a pneumatically actuated double-acting cylinder 62, an upper probe housing 64 that contains a linear voltage differential transformer (LVDT) 66, and a lower probe housing 68 which includes a spring biased indenter pin assembly 70 that terminates at probe tip 20 and houses an indenter pin for engaging an underlying test part 72.

Bracket 60 is essentially in the shape of a section of channel including a vertically oriented portion 60a that is supportively affixed to base 14, an upper horizontally disposed portion 60b that cooperates with the top 24 of assembly 18 and a lower horizontal wall portion 60c which guides the vertical reciprocation of the upper probe housing 64. A height adjustment assembly at top 24 includes a vertically oriented threaded shaft 76 cooperating with an internally threaded and externally knurled sleeve 78 which in turn is journaled for rotation about a vertical axis by a ball bearing assembly 80. The inner race of assembly 80 is joined to sleeve 78, and the outer race is fixedly seated in an opening provided for the purpose in bracket portion 60b. The lower end of shaft 76 extends downwardly through sleeve 78 and is joined at the lower end to a disc shaped mounting flange 82 which in turn is fastened to an upper axial end of the double-acting pneumatic cylinder 62 by screw fasteners 84. With this construction, the outer knurled surface of sleeve 78 may be rotated between the thumb and index finger so as to cause shaft 76 to be translated up or down and hence to cause a likewise vertical position adjustment of cylinder 62 and the upper and lower probe housings 64 and 68, respectively, attached thereto.

Internally of cylinder 62 is a piston head 86 and an associated vertically reciprocating single ended piston rod 88 the lower end of which is fixedly attached to the upper probe housing 64 by a threaded connection indicated at 90 and a locknut 92. When the probe is retracted (position shown), a lower cylinder port 94 is pressurized while the upper port 96 is exhausted. To drive the probe assembly in an impact stroke, the pressurization and venting of ports 94 and 96 is reversed.

To selectively pressurize and vent ports 94 and 96, an electrically piloted pneumatic control 98 is provided as schematically shown in FIG. 2. Control 98 includes a conventional, solenoid piloted, 4-way, 2-position valve 100. An electrically operated solenoid pilot valve 102 located at an end of valve 100 responds to a control signal S1 to selectively and alternately connect ports 94 and 96 to a source of pressurized air indicated at 106, with the unpressurized port being connected to an exhaust vent indicated at 108. Valve 100 and pilot valve 102 are biased to the retract mode position shown in FIG. 2 and are responsive to a signal S1 to shift valve to the impact test mode shown by the dotted line position of valve 100.

The source of pressurized air 106 is communicated to the ports of cylinder 62 over a branched pressurized line 110 and hence through valve 100 to ports 94 and 96. The exhaust vent 108 is communicated with the cylinder via exhaust lines 112 and 114 which include the serial connection of separate, independently adjustable flow control valves 116 and 118, respectively. Flow control valves 116 and 118 are separately adjusted to provide independent control over the rate of the downstroke which causes the indenter tip to impact the test part, and the rate of retraction of the indenter probe when it is withdrawn from the part at the end of the test cycle. The independently adjustable impact and retraction stroke rates is significant when testing parts which have a rate dependent hardness, i.e., the amount of resistance to penetration of the indenter pin varies as a function of the speed at which the indenter tip is forced into the test part.

The upper probe housing 64 is of tubular shape and the outer cylindrical wall thereof slidably cooperates with the inside diameter of a bushing 120 congruently mounted to a circular hole provided in bracket portion 60c for the purpose of guiding the vertical reciprocation of the probe. Bushing 120 may be made of a low friction synthetic material such as polytetrafluoroetlylene. The outside diameter of probe housing 64 adjacent its lower end 122 is reduced and is provided with exterior threads that cooperate with interior threads formed on the inner circumferential wall 124 of the lower probe housing 68. A locknut 126 secures the probe housings 64 and 68 in place once they have been threaded together to a desired lengthwise position.

LVDT 66 is mounted adjacent the lower end of probe housing 64 and includes a stationary winding section 66a and a movable ferromagnetic core 66b. The winding section 66a includes primary and secondary windings and is affixed to the interior circumferential wall of probe housing 64 so that core 66b is movable relative thereto by reason of the connection of core 66b to a movable plunger element of the indenter pin assembly 70.

The spring biased indenter pin assembly 70 is per se conventional and the parts therefor may be obtained from the Barber-Coleman Company of Rockford, Ill. Assembly 70 includes a plunger 130 having a vertically oriented upper stud-like portion 130a that supports a coaxial, slender, upwardly projecting connective rod 130b, the upper end of which mounts the ferromagnetic core 66b. A mid-body portion of plunger 130 is enlarged to form a flange 130c, the lower face of which abuts against an upper axial end of a threaded, hollow pin guide 132. The lower end of plunger 130 has a coaxial stud portion 130d that projects downwardly into a mating counter bore in the pin guide 132 so that the lowermost end of plunger portion 130d strikes an upper end of the indenter pin 134, which is slidably retained within a center guide bore of guide 132. The lower end of pin 134 is pointed and although not shown by the drawings, an interference fit between the pointed end of pin 134 and the central bore of guide 132 at probe tip 20 holds the pin within guide 132 while allowing the pin tip 136 to protrude from the guide for penetrating test part 72. A helical compression spring 137 is coaxially disposed about plunger 130a and is held in compression between an upper face of the enlarged flange portion 130c of the plunger and a lower axial face of an annular calibration nut 138 which threadedly cooperates with the interior threads of the lower probe housing 68.

By adjusting the relative lengthwise position between calibration nut 138 and the indenter pin guide 132 which is also threadedly engaged with the interior of probe housing 68, the amount of compressive force associated with spring 137 and hence the magnitude of the impact force transmitted to pin 134 by the downwardly stroked head assembly 18 is adjustable to calibrate the depth of penetration of indenter pin tip 136 into a standard of known hardness. Once the compression force on spring 137 has been satisfactorily adjusted, the longitudinal position of pin guide 132 relative to the lower probe housing 68 and calibration nut 138 is fixed by tightening locknut 140 which is threaded onto guide 132 and engages the lower axial end of housing 68.

After the probe has been calibrated in the foregoing manner, the output signal from LVDT 66 is zeroed by loosening locknut 126 at the upper end of probe housing 68 and then threadedly adjusting housing 68 relative to housing 64 until the LVDT core 66b is moved to a position relative to the stationary windings 66a that produces a zero or other desired nominal electrical output from LVDT transducer 66.

With reference to FIG. 3, the internal circuitry of hardness testing apparatus 11 is shown to include a microprocessor-based computer 150, circumscribed by the dotted line. Computer 150 is interfaced through various buffer circuits to receive an analog-to-digital converted hardness signal from LVDT transducer 66 and to output control and data signals to the various numerical displays and warning indicators.

More particularly as shown in FIG. 3, LVDT transducer 66 is connected to a modulator/demodulator circuit 152 which is coupled over connections 154 to primary and secondary windings (not specifically shown) of transducer 66 in a known manner so as to cause a modulated AC signal applied to the primary winding to be differentially coupled to the transducer's secondary winding in response to relative displacement of the ferromagnetic core 66b (FIG. 2). The differential coupling of the AC signal from the primary to secondary windings is in turn internally processed by circuit 152 to develop a varying level DC signal at an output 156 that fluctuates in accordance with relative movement of core 66b, and hence has a function of the penetration of tip 136 of indenter pin 134 into test part 72. The change in level of the DC signal at output 156 hence is representative of the hardness of the test part. This varying DC signal is modified by a gain and zero adjust circuit 158 so as to scale the magnitude of the signal (by varying its gain) and so as to set the level of the signal to zero to correspond to zero displacement of the pin tip (by the means of the zero adjust portion of circuit 158).

The output signal from circuit 158 is thus the analog of the material hardness and this analog hardness signal digitized by an analog-to-digital (A/D) converter 162. An eight-bit parallel digital word is thus produced at an output 164 representing the digitized hrdness signal originating at transducer 66 and circuit 152, and this eight-bit hardness word is fed through a buffer 166 to an input port of computer 150 as described more fully below. Associated with the eight-bit hardness word on output 164, is an end of conversion (EOC) signal produced on converter output lead 168 to signal the end of an analog-to-digital conversion operation and announce to the computer that the contents of converter 162 have stabilized and may now be accepted via buffer 166.

The two digit alpha-numeric display 38 is connected to an output port in chip 186 of computer 150 and as mentioned above displays a two digit hardness number in Barcol units. It also displays certain letter and symbol codes in connection with the semi-automatic recalibration mode of the apparatus as described more fully herein.

The lower and upper limit thumbswitches 44 and 46, respectively (see also FIG. 1), have multibit outputs 170 and 172 which carry binary coded decimal (BCD) signals representing the two digit lower and upper limits that have been set on switches 44 and 46, respectively. The limit BCD signals are fed from outputs 170 and 172 through a limit switch selector to an input port in chip 186 of computer 150, as described more fully below.

An output port in chip 186 of computer 150 selectively and automatically operates a set of control line drivers 174 in response to the herein described processing routines of computer 150. In turn, drivers 174 selectively energize audible alarm 48, low and high alarm lamps 40 and 42, respectively, parts counter and display 50 and pneumatic cylinder control 98. Each test cycle is actuated by either fence mounted microswitch 30, or a panel mounted switch 36. These switches as shown in FIG. 3 are connected in parallel between ground and a trigger input 176 of a one shot multivibrator 178 having an adjustable time-out period. The output of one shot multivibrator 178 is connected to an input port chip 186 of computer 150 to initiate the various processing routines thereof that are automatically executed during each test cycle.

Down count switch 52 is connected between ground and an input port of chip 186 of computer 150 for decrementing parts counter and display 50 as described above in connection with FIG. 1.

With more specific reference to the microprocessor-based computer 150, it is shown in FIG. 3 to include: an eight-bit integrated circuit microprocessor 180 and an associated external timing crystal 182; an erasable programmable read only memory (EPROM) and input-/output (I/O) integrated circuit chip 184; a static random access memory (RAM), I/O and timer integrated circuit chip 186; a logic select (decoder) chip 188; and a limit switch selector chip 190.

In this particular embodiment, computer 150 uses compatible large scale integrated circuit chips avaiable from Intel Corporation of Santa Clara, Calif. including an 8085 for microprocessor 180, an 8205 for logic select chip 188, an 8755A for EPROM and I/O chip 184, an 8155A for static RAM, I/O and timer chip 186, a pair of back-to-back connected buffer chip LS240 for limit switch selector 190, and an LS240 for buffer chip 166.

Microprocessor 180 communicates with the logic circuitry of chips 184 and 186 over a control bus 192 and an address/data bus 194 with the assistance of logic select chip 188. The timer section of chip 186 performs an automatic interrupt function for causing the apparatus to be recalibrated after a predetermined, fixed period of operation. For this purpose, chip 186 has a timer interrupt output connected over lead 196 to an interrupt input of microprocessor 180. As described more fully hereinafter in connection with the flowchart of FIGS. 5a-5f and 6, a timer interrupt signal on lead 196 causes the apparatus to automatically jump at predetermined clock times to service a recalibration routine.

With reference to FIG. 4, two timing waveforms are illustrated in which the top waveform shows a low going output pulse from one shot multivibrator 178, and the bottom waveform depicts a high going logic signal representing the operation of pneumatic cylinder control 98 during the impact stroke of probe head assembly 18. With the apparatus in a quiescent condition, the output from one shot multivibrator 178 is high. In response to operation of either the fence mounted switch 30 or the panel mounted switch 36 at a time to the output of multivibrator 178 swings low as shown in FIG. 4, and remains low until the multivibrator times out at a time $t_2$, whereupon the waveform returns to its normal high level. In response to the low going output from multivibrator 178, microprocessor 180 of computer 150 acts through chip 186 and control line drivers 174 to actuate pneumatic cylinder control 98 at a time $t_1$ whereupon the rising waveform shown in FIG. 4 represents the start of the down or impact stroke of probe head assembly 18. At a time $t_2$ when one shot multivibrator 178 times out, the probe head assembly 18 has stabilized on test part 72 (FIG. 2). Thus the high going trailing edge of the output of multivibrator 178 signals microprocessor 180 that data acquisition can commence and as described more fully hereinafter in connection with the flowchart of FIGS. 5a-5f, the analog-to-digital converted hardness signal is now received and processed by computer 150. By delaying the data acquisition until time $t_2$, any bouncing or instability of the probes spring biased pin assembly 70 (FIG. 2) has died out and the displacement of the indenter pin measured by LVDT transducer 66 can now be used to accurately reflect the depth of penetration of pin tip 136. Subsequently at time $t_3$ in the diagram of FIG. 4, the data acquisition has been completed and pneumatic cylinder control 98 is operated to cause valve 100 (FIG. 2) to retract head assembly 18 from the part.

FIGS. 5a-5f together constitute a flowchart of a presently preferred embodiment of test apparatus 11, by which microprocessor 180 is programmed to carry out a sequence of signal processing routines.

With reference to FIG. 5a, microprocessor 180 of the testing apparatus is programmed to start either in response to power up, or if already on, then in response to operation of reset switch 54. When so started, a first instruction block 200 initializes the computer 150 variables and the associated I/O ports. Upon completing these initialization operations, a series of instruction and decision blocks provide a calibration processor which involves two degrees of recalibration. A first degree of recalibration is provided by comparing the measured hardness of a calibration block with the actual and known value of hardness stored in memory, and then storing the difference (error) for automatically correcting subsequent test measurements. A second degree of recalibration is called for when the difference or error of apparatus 11 exceeds a predetermined threshold, and in such case the instrument is shut down and the operator is instructed to carry out major recalibration servicing involving, among other things, the possible replacement of the indenter pin 134 and/or the adjustment of pin biasing spring 137 (FIG. 2).

This calibration processing commences with an instruction block 202 by which the audible and visual alarms are temporarily disabled. Next, an instruction block 204 causes the code letters "CA" to be presented on the two digit alpha-numeric hardness display 38 (FIGS. 1 and 3). The code letters "CA" instruct the operator to place a calibration block under the probe head assembly 18 (FIG. 2) in lieu of a test part 72 of unknown hrdness. The placement of the calibration block causes microswitch 30 to be operated in the same manner as occurs in response to the placement of test part 72 under the probe as described above, and a test cycle is thereby triggered. More particularly, a decision block 206 determines whether the calibration block is in place by checking the electrical condition of one shot multivibrator 178 (FIG. 3). If the status of one shot multivibrator 178 remains high (refer to FIG. 4) then the decision by block 206 is negative and the processor loops back and continues testing for the status of the multivibrator output. If on the other hand the multivibrator output has gone low, indicating that the calibration block is in place, then an affirmative decision from block 206 advances the program to the next instruction block 208 which engages the pneumatic cylinder by causing pneumatic control 98 to drive probe head assembly 18 downwardly in an impact stroke. The activation or engagement of pneumatic cylinder control 98 and cylinder 62 in response to instruction block 208 is alternatively referred to as loading of the probe head.

After pneumatic cylinder 62 has been actuated in an impact stroke, a decision block 210 of the calibration processor tests for the probe head being loaded and stable. The stabilization of the probe head is assumed to occur after a fixed interval following the operation of the pneumatic cylinder, and as described above in connection with FIG. 4, this fixed delay interval is measured by the time-out interval of one shot multivibrator 178 between its low going leading edge at $t_0$ to its rising trailing edge at $t_2$. Thus, after the time interval $t_2$, it is assumed that the probe tip 20 of head assembly 18 has stabilized on the calibration block and an affirmative decision from instruction block 210 advances the calibration processing onto a series of instruction blocks that cause the apparatus to measure the hardness of the calibration block.

Figure 5B:
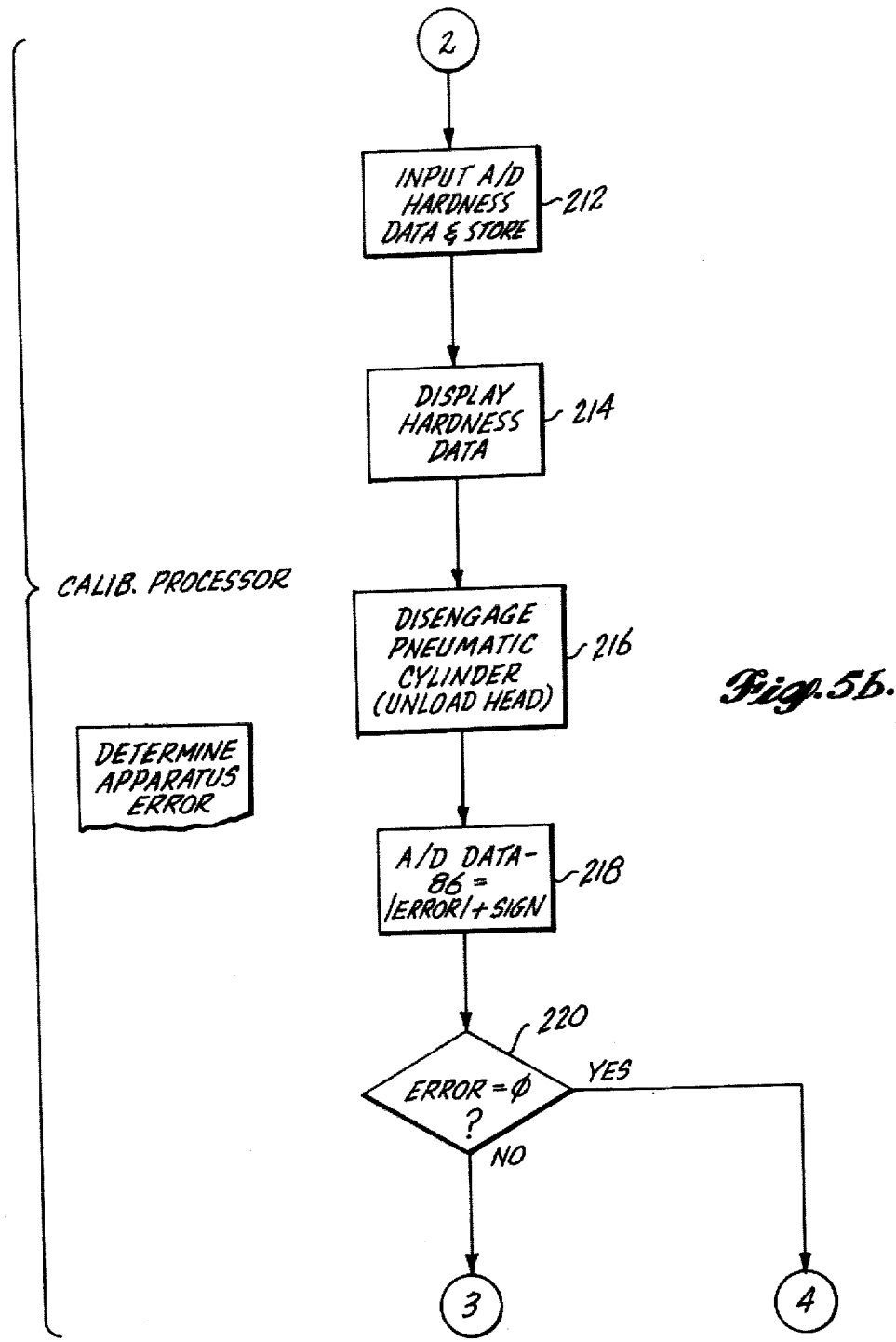

More specifically, the affirmative output from decision block 210 continues (connective notation 2) on over to FIG. 5b where an instruction block 212 causes the eight-bit digitized hardness measurement from A/D converter 162 (FIG. 3) to be transferred from converter 162 through buffer 166 into computer 150 through an input port of chip 184. The hardness measurement of the calibration block is thus fed into computer 150 and stored in a temporary memory therewithin. Next, the measured hardness value is presented on two digit display 38 by instruction block 214 and a succeeding instruction block 216 effects disengagement of the probe head assembly 18, by causing pneumatic cylinder control 98 (FIG. 2) to be piloted in a retraction stroke of the probe head assembly. Hence the probe head becomes unloaded.

The instrument error is now determined by executing the instruction in block 218 which causes the measured hardness value to be subtracted from the known hardness of the calibration block, which in the present example has a hardness of 86 in Barcol units. The resulting difference, if any, is made available in the form of the absolute value of the error (magnitude) and the sign (plus or minus) indicating whether the measured hardness is greater or less than the actual hardness of the calibration block.

Figure 5C:
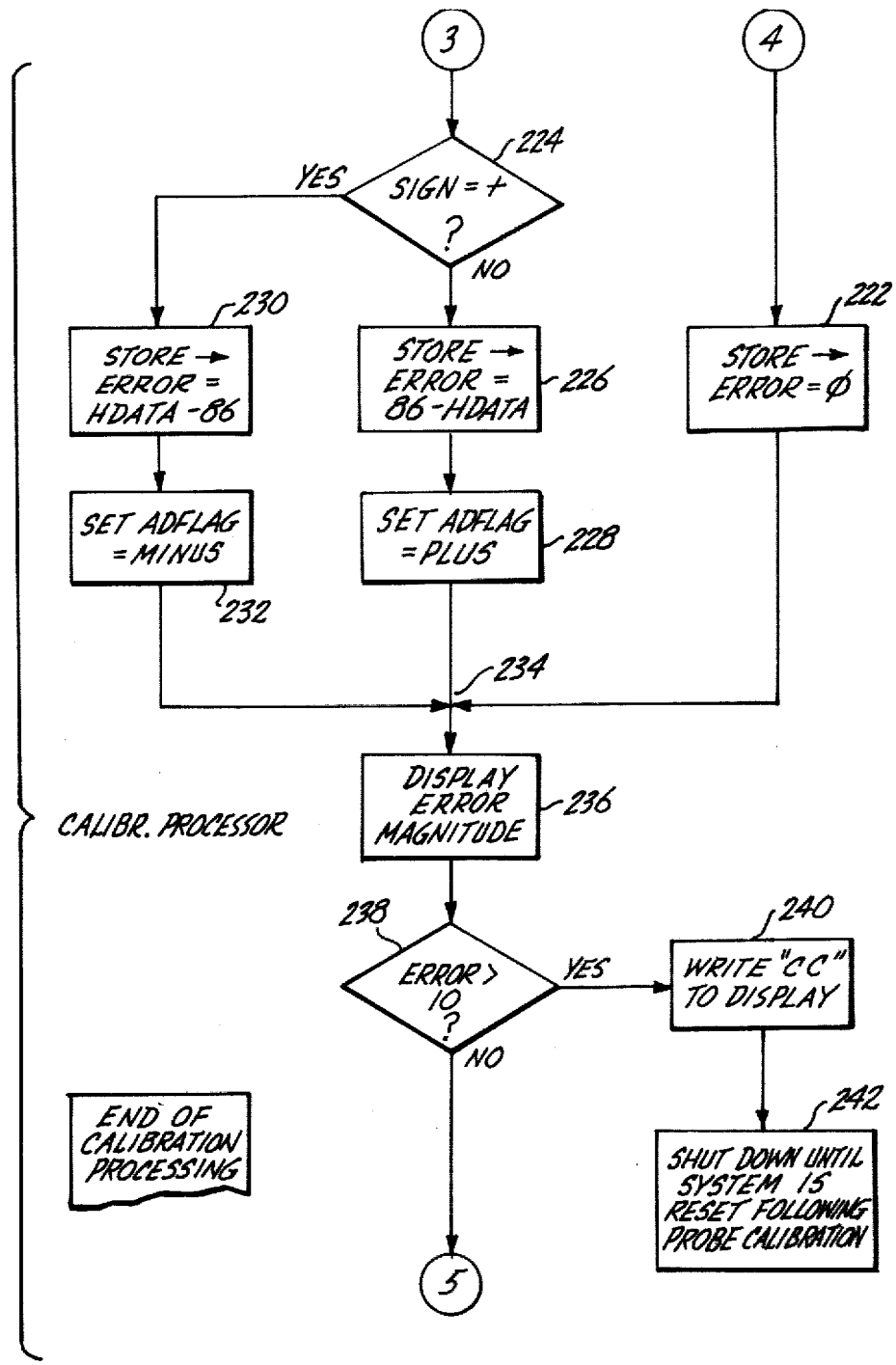

If the error is equal to zero, indicating that no further calibration or measurement correction is required, then a block 220 produces an affirmative decision and the program proceeds as indicated (connective notation 4) to FIG. 5c. In FIG. 5c, an instruction block 222 causes the determination of zero error to be stored for subsequent processing.

If, on the other hand, back in FIG. 5b, decision block 220 determines that the error is not equal to zero, which is more typical, then a negative decision from block 220 advances the program (connective notation 3) to FIG. 5c where a decision block 224, causes the program to branch to either a first series of instruction blocks 226 and 228, or a different series of instruction blocks 230 and 232. Collectively these decision and instruction blocks quantify the error by storing its value and sign so as to be available for correcting each subsequent measurement of a test part of unknown hardness. Thus if block 224 determines that the error sign is plus (representing a condition in which the measured hardness exceeds the known hardness of the calibration block), then decision block 224 produces negative output and causes instruction blocks 226 and 228 to compute the magnitude of the error by subtracting the measured value from that of the known calibration block. Also, a parameter termed adflag is set to plus so that the error will be added to any subsequent hardness measurement. Conversely, an affirmative decision from block 224 causes instruction blocks 230 and 232 to compute the magnitude of the error and set the parameter adflag to minus so as to effect the subtraction of the error from each subsequent hardness measurement.

The outputs from all of the foregoing branches of the error computation processing are recombined at 234 and the program proceeds to instruction block 236 which causes the computed error magnitude to be displayed on the two digit hardness display 38 (FIGS. 1 and 2).

Subsequent to the display of the error magnitude by instruction block 236, a decision block 238 tests for whether the magnitude of the error exceeds a predetermined threshold deviation. In this embodiment, the threshold deviation is selected to be plus or minus 10 points on the Barcol scale. Thus, block 238 determines whether the computed error is greater than a magnitude of 10. If not, then the programmed apparatus is caused to advance (connective notation 5) to the start of the main data acquisition processing routine shown in FIG. 5d, wherein test parts of unknown hardness are measured.

Alternatively, and with further reference to FIG. 5c, a determination by block 238 that the error does exceed the predetermined threshold deviation of 10 points, causes the programmed apparatus to execute instruction block 240 which causes the letter code "CC" to be written on hardness display 38 (FIGS. 1 and 3) to signify to the operator that the apparatus is out of calibration by an excessive amount. In such cases, a succeeding instruction block 242 causes the apparatus to be shut down until it is reset after the instrument has received major recalibration servicing, as described hereinabove.

Following major recalibration such as by readjusting of the probe biasing spring 137 of probe tip assembly 70 (FIG. 2), the operator resets the apparatus by operating switch 54 which returns the apparatus program to the starting point, where the operating sequence of the apparatus must again advance through the calibration processing as described above starting with instruction block 202 shown in FIG. 5a. Assuming that the physical readjustment of the indenter probe or other servicing, reduces the instrument's error to zero or less than the maximum permitted deviation of ±10 points, then the ensuing pass through the calibration processing section of the program will produce a negative decision at block 238 of FIG. 5c which causes the apparatus to proceed onto the start of the main data acquisition routine shown in FIG. 5d.

Figure 5D:
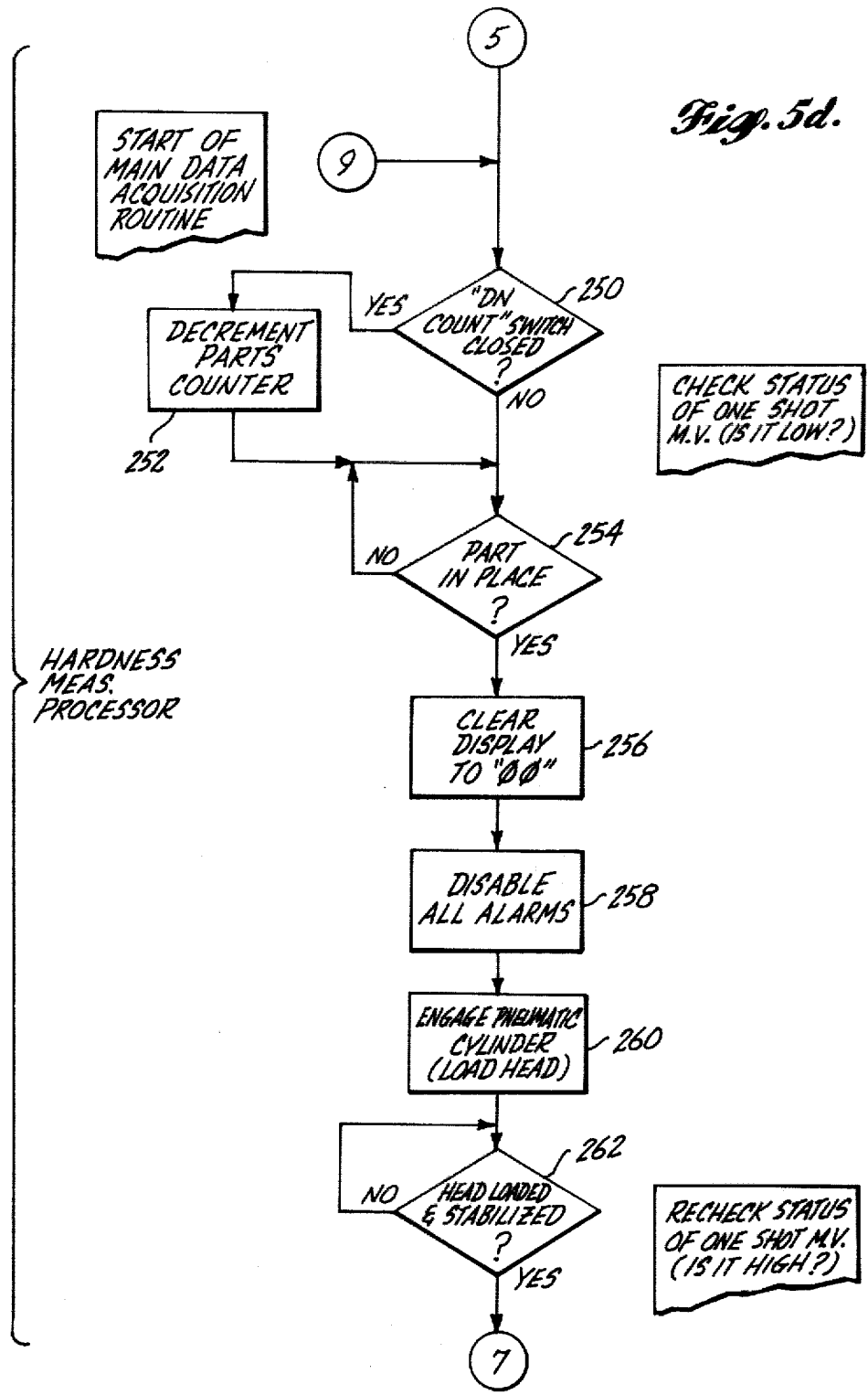

With reference to FIG. 5d, the hardness measuring processor includes a decision block 250 and an associated instruction block 252 which together provide for decrementing the parts counter and display 50 (FIGS. 1 and 3) in response to the condition of down count switch 52. When switch 52 is closed, an affirmative decision from block 250 causes instruction block 252 to decrement the count and return the flow to a point downstream of block 250.

The apparatus is now ready to test a part. A decision block 254 functions in the manner described above in connection with decision block 206 to determine from the status of one shot multivibrator 178 (FIG. 3) whether the test part 72 (FIG. 2) has been inserted into testing position beneath probe head assembly 18. Following block 254, an instruction block 256 clears hardness display 38 (FIGS. 1 and 3) to "00." Then instruction block 258 causes the audible and visual alarms to be temporarily disabled during this phase of the test cycle. Pneumatic cylinder control 98 is now operated by an instruction block 260 to engage pneumatic cylinder 62 for driving head assembly 18 (FIG. 2) downwardly in an impact stroke as described hereinabove. When probe tip 20 of assembly 18 reaches the test part and embeds tip 136 of indenter pin 134 into part 72 (FIG. 2) the head is considered to be loaded. A decision block 262 in FIG. 5d tests for a condition in which the head is loaded and has stabilized by rechecking the status of one shot multivibrator 178 in the same manner as described above in connection with decision block 210 of the calibration processor shown in FIG. 5a. When block 262 determines by an affirmative decision that the head has stabilized, then the flow of the program proceeds (connective notation 7) to FIG. 5e where instruction blocks 264 and 266 sequentially cause the selection and storing of low and high hardness limit values from the particular settings of thumbswitches 44 and 46 (FIGS. 1 and 3).

Next, an instruction block 268 causes the hardness signal measured by LVDT transducer 66 and converted to digital form by A/D converter 162 to be entered and stored in a memory section of computer 150 through buffer 166 and an input port of chip 184 (FIG. 3). The thusly stored hardness value (HData) represents a raw, uncorrected output of the LVDT transducer 66 and therefore, following block 268, a series of decision and instruction blocks effect an automatic error correction using the previously stored error developed during the calibration processing described above in connection with FIGS. 5a-5c. Accordingly, in FIG. 5e, a decision block 270 tests for adflag=plus, representing a condition in which the previously measured and stored calibration error is to be added to HData. An affirmation decision from block 270 causes an instruction block 272 to correct the hardness measurement by setting HData=HData+error and causing the sum to be stored as corrected HData. A negative decision from block 270, representing a condition in which the error is to be substracted from the raw, uncorrected HData, causes an instruction block 274 to set HData=HData−error and to store the result as corrected HData. The flow paths from instruction blocks 272 and 274 merge and lead to a display instruction block 276 which causes the corrected HDATA hardness value to be presented on the two digit hardness display 38 (FIGS. 1 and 3), and then the program flow path extends from FIG. 5e (connective notation 8) to FIG. 5f.

The hardness measuring processor includes as shown in FIG. 5f, one further instruction block 278 which operates pneumatic cylinder control 98 (FIGS. 2 and 3) to disengage or unload the probe head assembly 18 by operating cylinder 62 in a retraction stroke.

Following the retraction of the probe head, the flowchart as shown in FIG. 5f continues into a processing section that compares the measured and error corrected hardness with the preset low and high limits and that counts each tested part which falls within acceptable limits. This out of limits hardness check includes an initial instruction block 280 which fetches the low limit previously set on thumbswitch 44 (FIGS. 1 and 3) and also fetches the corrected hardness data (HData) for comparison. A decision block 282 compares the corrected HData with the low limit and if the corrected HData is less than the preset low limit, an affirmative decision results in the activation of the low alarm lamp 40 (FIGS. 1 and 3) by means of low alarm lamp instruction block 284. A negative decision from block 282, indicating that the low limit has not been exceeded, causes the program to test the corrected Hdata with the high limit in a decision block 286. If the high limit has been exceeded, an affirmative decision from block 286 activates the high alarm lamp 42 (FIGS. 1 and 3) in accordance with instruction block 288. If either of the lamp alarm instruction blocks 284 or 288 is activated, the alarms horn is also activated for 0.5 seconds by instruction block 290.

A negative decision from the high limit comparison block 286 causes parts counter block 292 to increment counter and display 50 one count. It is observed that the output of alarm instruction blocks 284, 288 and 290 rejoins the program flow downstream of parts counter block 292 so taht in this particular embodiment, only parts tested and found acceptable are counted on the counter and display 50. Instruction blocks 290 and 292 complete the limits check and part counting processing and the program flow then loops back to the beginning of the main data acquisition section of the flowchart (connective notation 9) where it rejoins the flowchart at the top of FIG. 5d. So long as the recalibration time interrupt remains quiescent and allows the main data acquisition routine of the system to continue, the processors will continue to circulate in the hardness measuring processor and limits check and parts counting processor sections without reverting back to the calibration processing of FIGS. 5a-5c.

With reference to FIG. 6, the recalibration time interrupt processor automatically keeps track of the operating time of the apparatus and after a predetermined operating period, stops the above-described signal processing shown in the flowcharts of FIGS. 5a-5f to provide for recalibration of the apparatus. In particular, the recalibration interrupt processor includes an initial instruction block 300 which causes the contents of all the registers, memories and other variables of the microprocessor-based computer 150 to be saved during the interrupt processing. Next, an instruction block 302 increments an internal counter by one count which in effect is a time keeping device. The internal counter is incremented in this manner at a known clock rate determined by the particular design of computer 150. In this particular embodiment, the incrementing clock rate is once every 5.3 milliseconds. Using this clock rate, and a chosen recalibration time period, for example, 60 minutes as used in the presently disclosed embodiment, a total count is determined which will cause a decision block 304 to time-out at the chosen recalibration time-out period. Thus, at the incrementing rate of 5.3 milliseconds, a count of 679,245 is equivalent to 60 minutes. So long as the count accumulated pursuant to instruction block 302 remains less than the equivalent of 60 minutes, decision block 304 will continue to produce a no response for each pass through the interrupt routine which will occur every 5.3 milliseconds. The no decision from block 304 causes an instruction block 306 to return to the main processing loop of the program to a location at which the processing had been interrupted in order to service the interrupt routine.

When decision block 304 determines that the count pursuant to counter block 302 has attained the equivalent of the recalibration time-out period, an affirmative decision. by block 304 diverts the interrupt routine down to a series of instruction blocks 308, 310, 312 and 314. Collectively these instruction blocks cause two dashes, " - - ", to be written onto the hardness display 38 (FIGS. 1 and 3) in which the dashes are on for 0.5 seconds and off for 0.5 seconds. This intermittent flashing of two dashes on display 38 continues until the apparatus is reset by operating reset switch 54, which is described above, returns the program to the initialization and calibration processing described above and shown by FIGS. 5a, 5b and 5c.

Figure 5E:
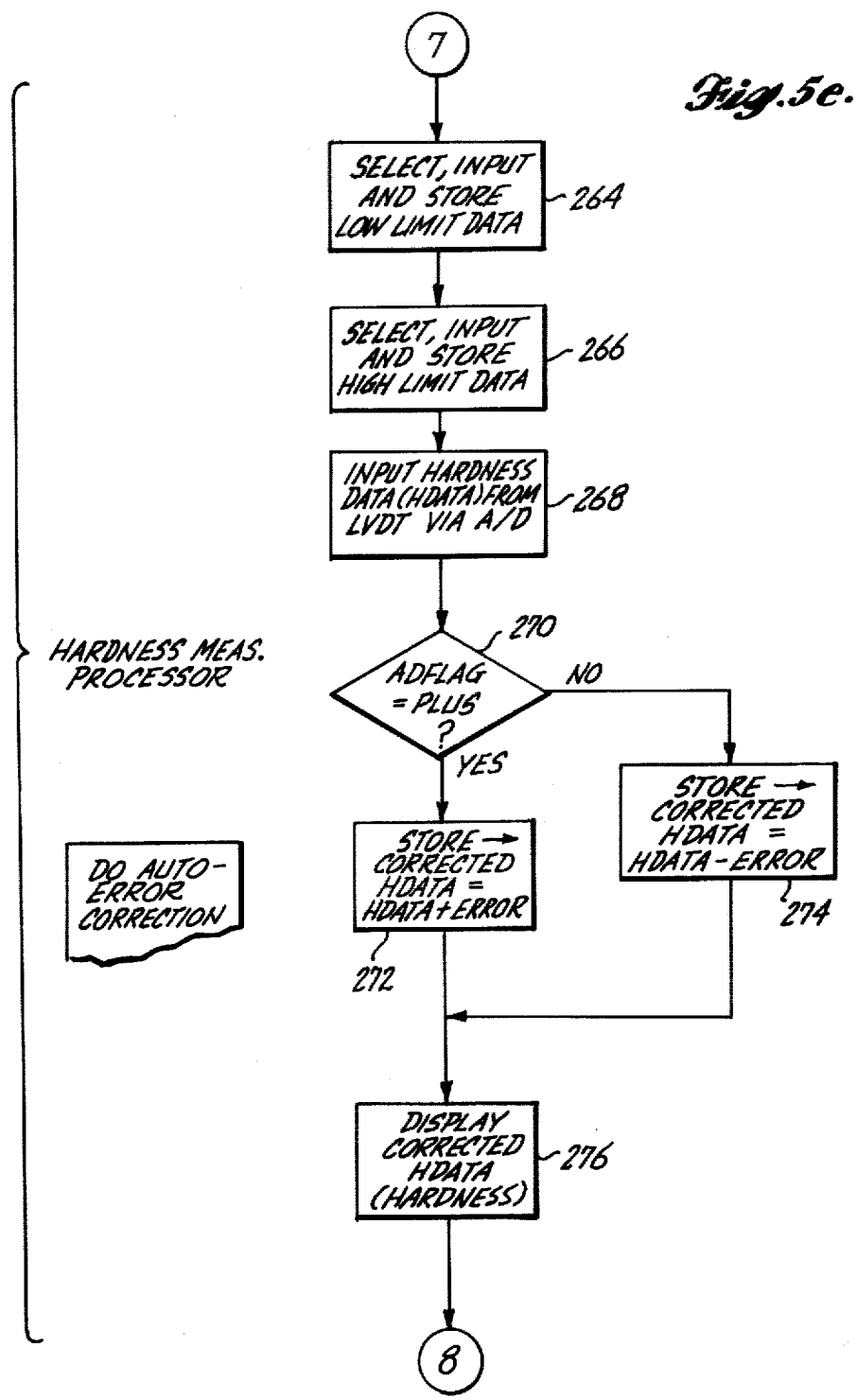

After the apparatus is reset by switch 54, and recalibrated, either pursuant to the first level of calibration in which the apparatus automatically corrects for errors less than plus or minus 10 points, or pursuant to the higher degree of calibration in which the apparatus undergoes major calibration servicing, the processing by computer 150 will enter the main data acquisition routine and the associated hardness measuring processing shown by the flowchart in FIGS. 5d through 5f. The main data acquisition routine will continue to process test cycle data until the apparatus is subsequently interrupted when the recalibration time interrupt routine again times out at 60 minutes, or some other chosen time-out period.

Operation

The measurement of material hardness is known to be useful in quality control testing of metals and other structural materials. For example, certain metal alloys such as aluminum are tested for composition and temper by a twofold test involving measurement of both the conductivity and hardness of the aluminum part. The strength and other physical characteristics of aluminum alloys can vary significantly depending upon the proportions of base metals that compose the alloy. The twofold testing for conductivity and hardness has heretofore been found to be a reliable indication of the composition and temper of the aluminum alloy. The one step, indenter-type hardness testing apparatus 11 in accordance with the foregoing disclosure has proven to be effective in the rapid testing of aluminum alloy parts for the hardness component in connection with the foregoing twofold quality control test.

To prepare apparatus 11 for testing a batch of parts, switch 54 (FIG. 1) is operated to reset the registers and other variables associated with computer 150. The height of head assembly 18 is adjusted using manually rotatable sleeve 78 (FIG. 2) to place the lower tip 20 of the probe within striking distance of a calibration block used for calibrating the apparatus. In this particular embodiment, piston 86 and the associated rod 88 thereof has a travel of approximately one-half inch such that sleeve 78 is adjusted to place probe tip 20 within one-half inch of the upper surface of the calibration block or test part, as the case may be.

Having operated the reset switch 54, computer 150 causes display 38 to present the code letters "CA" in accordance with the above-described operation of the calibration processor. This signals the operator to proceed with the calibration test and with the calibration block of known hardness in place, either fence mounted switch 30 or panel mounted switch 36 is operated to initiate the calibration test cycle. The hardness is read and compared with the known hardness of the calibration block, and as described in greater detail above, if the error between the measured hardness and that of the calibration block is excessive, for example greater than the plus or minus 10 points, then the apparatus is disabled until it undergoes major calibration servicing. If on the other hand, the error is less than plus or minus 10 points, reflecting a minor out of calibration condition, then the apparatus is enabled to proceed with routine testing of parts and the magnitude of the error and its sign are stored and used to automatically correct the raw hardness measurement.

Assuming that the calibration processing reveals a error less than plus or minus 10 points, the apparatus 11 is now ready for testing parts, and the height of probe head assembly 18 is readjusted as necessary by using rotatable sleeve 78 as described above. The test parts are now placed in succession under the probe head assembly 18, each time causing fence mounted switch 30 to trigger an automatic test cycle. For each cycle, the hardness of the test part is measured, the error automatically corrected, and the resulting corrected hardness value displayed on the two digit alpha-numeric display 38 (FIG. 1). Alternatively, a test cycle may be initiated by pressing test switch 36 on panel 34, such as where the test part has a shape that makes it impractical or impossible to actuate fence mounted microswitch 30.

The hardness measuring processor section of computer 150 shown in FIGS. 5d–5f compares the corrected hardness value (corrected HData with the low and high limits set on thumbswitches 44 and 46 shown in FIG. 1. If the test part measures outside the limits, the appropriate one of alarm lamps 40 and 42 is turned on and the alarm horn 48 is sounded (FIG. 1). If the part tests within the preset limits, then none of the alarms sound and the part is counted by incrementing counter and display 50 on panel 34 (FIG. 1). The testing of parts proceeds in this manner until the operator finishes the test batch, or until the recalibration interrupt routine, the flowchart for which is shown in FIG. 6, stops the normal testing sequence to require a calibration check. The recalibration interrupt is indicated to the operator by the flashing symbols " - - " on the alpha-numeric hardness display 38. The flashing " - - " display continues until the apparatus is reset by operating reset switch 54 on panel 34 (FIG. 1). When reset, the programmed computer jumps to the start of the flowchart and commences the recalibration processing as shown in FIGS. 5a–5c and described in detail hereinabove. Thus the symbols "CA" are now displayed on alpha-numeric display 38 to signify that the apparatus is in the calibration mode, and responsively, a calibration block of known hardness is placed under the probe and the calibration checked. If the calibration check shows an error of less than the pre-established threshold ($\pm 10$ points), the apparatus is enabled to proceed with further routine testing.

However, for the purpose of example, let it be assumed that the calibration check reveals an excessive error, greater than plus or minus 10 points. This particular level of maximum permissible deviation or error has been selected in the disclosed embodiment to indicate to the operator that a major problem exists and that calibration servicing is required. The period of the timed recalibration interrupt of 60 minutes has been selected in the present embodiment to provide a reasonable compromise between the need to ensure accuracy for each individual test cycle and the competing need to minimize the down time of the apparatus.

A major calibration servicing may involve any one or more of a number of corrective steps. One such step may be to readjust the biasing spring 137 of the spring biased indenter pin assembly 70 as described more fully above in connection with FIG. 2. Another possible recalibration step is to replace the indenter pin 134 (FIG. 2) when visual inspection revelas excessive wear or fragmenting of tip 136. Another servicing step my require adjustment of the probe impact stroke so that the rate at which the probe is driven toward and into contact with the part is either excessively fast or excessively slow. As mentioned above, measuring the hardness of certain materials by an indenter-type instrument can produce inconsistent results if the material is sensitive to the rate at which the indenter tip is driven into the material. Some materials, such as aluminum alloys, are quite sensitive to variations in the speed of the probe at impact and in order to achieve consistent readings over a broad range of hardness values, it is necessary to adjust the impact rate of the probe. This is achieved as described in greater detail above, by adjusting the variable flow control value 116 of pneumatic valve 100 of cylinder control 98.

Moreover, for rapid testing of parts, it is desirable to retract probe head assembly 18 as rapidly as possible. This objective, together with the independent need to adjust the impact stroke rate, is met in the disclosed and preferred form of apparatus 11 by the provision of variable flow control valve 118, the counterpart to control 116, for adjusting the rate of the retraction stroke. More specifically, flow control 118 is adjusted independently of control 116, so that the retraction stroke rate can be increased to the maximum possible extent for rapid testing of parts, while leaving control 116 set at an empirically determined impact stroke rate that yields consistently accurate hardness measurements.

Once the major calibration servicing has been performed, the apparatus is reset by reset switch 54 (FIG. 4) and the apparatus is again checked by re-executing the calibration processing section shown in FIGS. 5a–5c. When the apparatus error is less than the predetermined maximum of plus or minus 10 points, only then is it enabled to proceed with routine testing of parts.

While only a particular embodiment has been disclosed herein, it will be readily apparent to persons skilled in the art that numerous changes and modifications can be made thereto including the use of equivalent means and devices without departing from the spirit of the invention.

The embodiments of the invention in which an exclusive property or privilege is claimed are defined as follows:

1. In a hardness testing apparatus of the type having an indenter probe and a probe actuator for controllably moving said probe into and out of contact with a test part to thereby cause said probe to deformably penetrate the test part, and having sensing transducer means for producing an electrical signal representing the degree of such penetration as a measure of the hardness of the test part, the improvement in signal processing circuitry of such hardness testing apparatus comprising:
   reset means;
   indicator means responsive to said reset means for indicating a calibration mode; and,
   calibration processor means responsive to actuation of said probe by said actuator, said calibration processor means comprising:
   calibration measuring processor means for developing a signal measurement representing the measured hardness of a calibrating material when such a calibrating material is contacted by said probe;
   difference taking processor means for taking the difference between said measurement signal and a stored hardness signal representing the known hardness of said calibrating material, and for developing a calibration error signal in response thereto;
   comparison processor means for comparing said error signal with a predetermined threshold;
   automatic error correcting processor means responsive to said comparison means when said error signal is less than said predetermined threshold for storing said error signal for automatically correcting subsequent hardness measurements of parts of unknown hardness; and,
   recalibration disablement processor means responsive to said comparison processor means when said error signal is greater than said predetermined threshold for disabling said apparatus from further testing, said disablement processor means including means for reenabling said apparatus in response to said reset means.

2. The hardness testing apparatus of claim 1 wherein said signal processing circuitry further comprises timing processor means responsive to said reset means for disabling said circuitry at the end of a predetermined calibration check period, said timing processor means maintaining said circuitry in a disabled state until reset by said reset means which thereby initiates a succeeding recalibration check period.

3. The hardness testing apparatus of claim 1 wherein said signal processing circuitry comprises a microprocessor-based computer incorporating said calibration processor means, and further comprising hardness testing processor means responsive to said automatic error correcting processor means of said calibration processor means for cooperating with said probe so as to measure the unknown hrdness of test parts, and recalibration interrupt processor means for disabling said hardness testing processor means at the end of a predetermined calibration check period.

4. The hardness testing apparatus of claim 1 wherein said probe actuator comprises:
   electro-mechanical means responsive to a control signal for driving said probe into contact with a test part in an impact stroke and then retracting said probe from such test part in a retraction stroke, said electro-mechanical means comprising means for independently adjusting the rates of movement of said probe in said impact stroke and in said retraction stroke.

5. The apparatus of claim 4 wherein said electro-mechanical means comprises an electrical signal piloted fluid control means having a first flow control valve means for adjusting the rate of said impact stroke of said probe and a second flow control valve means for adjusting the rate of said retraction strobe of said probe, said first and second flow control valve means being independently adjustable.

6. The hardness testing apparatus of claim 1 wherein said probe actuator comprises a fluid operated cylinder means to which said probe is supportively joined and further comprising support means for said probe and probe actuator, and probe position adjustment means adjustably connecting said cylinder means to said support means for adjustably positioning said probe actuator and said probe relative to a test part.

7. The hardness testing apparatus of claim 6 wherein said cylinder means includes a piston and said probe being fixedly joined to said piston for controlled reciprocation therewith.

8. The hardness testing apparatus of claim 7 wherein said position adjustment means comprises a manually rotatable screw means.

9. The apparatus of claim 6 wherein said support means comprises first and second spaced apart portions, said cylinder means being joined to said first portion by said position adjustment means and probe guide means mounted on said second portion for slidably guiding said probe in controlled reciprocation by said cylinder means.

10. A hardness testing apparatus comprising:
    an indenter probe means;
    a probe actuator means for controllably moving said probe means into and out of contact with a test part to thereby cause said probe means to deformably penetrate the test part;
    sensing transducer means for producing an electrical signal representing the degree of such penetration by said probe means as a measure of the hardness of the test part;
    hardness testing processor means responsive to said probe actuator means and said sensing transducer means for developing a measurement signal representing the hardness of a test part;
    manually operated reset means; p1 calibration processor means responsive to said reset means and to said probe actuator means and to said sensing transducer means, said calibration processor means comprising:
    calibration measuring processor means for developing a calibration measurement signal representing the measured hrdness of a calibrating material when such a calibrating material is contacted by said probe means;
    difference taking processor means for taking the difference between said calibration measurement signal and a stored hardness signal representing the known hardness of said calibrating material, and for developing a calibration error signal in response thereto;
    comparison processor means for comparing said error signal with a predetermined threshold;
    automatic error correcting processor means responsive to said comparison processor means, said automatic error correcting processor means storing said error signal for automatically correcting subsequent hardness measurements by said hardness testing processor means when said error signal is less than said predetermined threshold; and, disablement processor means responsive to said comparison processor means for disabling said hardness testing processor means when said error signal is greater than said predetermined threshold.

11. The hardness testing apparatus of claim 10 further comprising timing processor means responsive to said reset means for starting a predetermined calibration check period, said timing processor means including means for disabling said hardness testing processor means at the end of said predetermined calibration check period, said timing processor means maintaining said hardness testing processor means in a disabled state until reset in response to said reset means.

12. The hardness testing apparatus of claim 11 wherein said hardness testing processor means comprises circuitry in a programmed microprocessor-based computer, and wherein said timing processor means comprises an interrupt processor of said microprocessor-based computer.

13. The hardness testing apparatus of claim 10 further comprising test actuating switch means adapted to be operated when a test part is disposed so as to be contacted by said probe means, and wherein said probe actuator means and said hardness testing processor means are responsive to said test actuating switch means.

14. The hardness testing apparatus of claim 13 further comprising delay circuit means connected in circuit with said test actuating switch means and said hardness testing processor means, said delay circuit means delaying operation of said hardness testing processor means for a predetermined delay interval following operation of said test actuating switch means, whereby a hardness measurement signal is developed by said hardness testing processor means only after said probe means has stabilized following an initial impact with a test part.

15. The apparatus of claim 10 further comprising indicator means responsive to said reset means and said calibration processor means for indicating a calibration mode.

16. The apparatus set forth in claim 10 further comprising sequence processor means for enabling said hardness testing processor means only after said comparison processor means and said automatic error correcting processor means of said calibration processor means has responded to an error signal that is less than said predetermined threshold.

17. The hardness testing apparatus of claim 10 further comprising:
limit selector means for selecting a predetermined limit of hardness against which a measured hardness signal is to be compared;
limit comparison processor means associated with said hardness testing processor means for comparing a hardness measurement signal with a limit selected by said limit selector means; and,
alarm means responsive to said limit comparison processor means for signaling an alarm condition in response to a measurement hardness signal that falls outside of a limit selected by said limit selector means.

18. The hardness testing apparatus of claim 10 further comprising a tested parts counting processor means and an associated count display means, said tested parts counter processing means being responsive to said hardness testing processor means for accumulating a count in response to each hardness measurement signal developed by said hardness measurement processor means.

* * * * *